United States Patent [19]

Misawa et al.

[11] Patent Number: 5,693,396
[45] Date of Patent: Dec. 2, 1997

[54] PHTHALOCYANINE COMPOUNDS AND OPTICAL RECORDING MEDIA COMPRISING THEM

[75] Inventors: Tsutami Misawa; Kenichi Sugimoto; Taizo Nishimoto; Takeshi Tsuda; Keisuke Takuma, all of Kanagawa-ken, Japan

[73] Assignees: Mitsui Toatsu Chemicals, Inc., Tokyo; Yamamoto Chemicals, Inc., Yao, both of Japan

[21] Appl. No.: 753,173

[22] Filed: Nov. 20, 1996

Related U.S. Application Data

[63] Continuation of Ser. No. 575,754, Dec. 20, 1995, abandoned.

[30] Foreign Application Priority Data

Dec. 27, 1994 [JP] Japan .................. 6-324333

[51] Int. Cl.[6] .................................................. B32B 3/00
[52] U.S. Cl. .................. 428/64.1; 428/642; 428/644; 428/648; 428/913; 430/56; 430/83; 430/96; 430/135; 430/270.14; 430/270.15; 430/270.16; 430/495.1; 430/945
[58] Field of Search ............................ 428/64.1, 64.2, 428/64.4, 64.8, 913; 430/56, 83, 96, 135, 270.14, 270.15, 270.16, 495.1, 945

[56] References Cited

U.S. PATENT DOCUMENTS

| | | | |
|---|---|---|---|
| 5,391,461 | 2/1995 | Koioke et al. | 430/271 |
| 5,424,171 | 6/1995 | Yanagisawa et al. | 430/271 |
| 5,474,825 | 12/1995 | Okano et al. | 428/64.8 |
| 5,532,033 | 7/1996 | Yashiro | 428/64.1 |

FOREIGN PATENT DOCUMENTS

| | | |
|---|---|---|
| 58-224448 | 12/1983 | Japan . |
| 58-224793 | 12/1983 | Japan . |
| 61-25886 | 2/1986 | Japan . |
| 61-154888 | 7/1986 | Japan . |
| 61-197280 | 9/1986 | Japan . |
| 61-246091 | 11/1986 | Japan . |
| 62-39286 | 2/1987 | Japan . |
| 63-37991 | 2/1988 | Japan . |
| 63-39388 | 2/1988 | Japan . |
| 2-43269 | 2/1990 | Japan . |
| 2-55769 | 2/1990 | Japan . |
| 2-147286 | 6/1990 | Japan . |
| 2-296885 | 12/1990 | Japan . |
| 3-62878 | 3/1991 | Japan . |
| 6-279448 | 10/1994 | Japan . |
| WO88/06175 | 8/1988 | WIPO . |

*Primary Examiner*—Elizabeth Evans
*Attorney, Agent, or Firm*—Burns, Doane, Swecker & Mathis

[57] ABSTRACT

A near infrared light-absorbing dye comprising phthalocyanine compounds represented by the following formula (2):

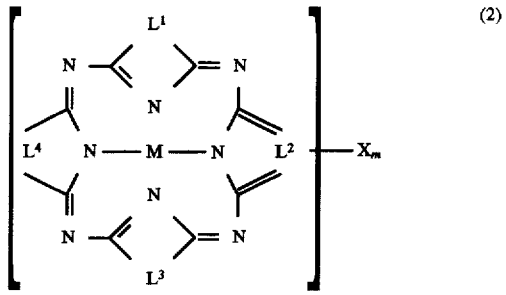

wherein in formula (2), M is two hydrogen atoms, a divalent metallic atom, a trivalent monosubstituted metallic atom, a tetravalent disubstituted metallic atom or an oxymetal atom, and $L^1$, $L^2$, $L^3$ and $L^4$ are each independently formula (a) or (b),

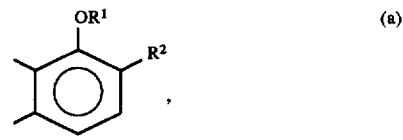

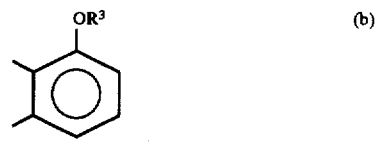

in the formula (a) or (b), $R^1$ and $R^3$ are each a substituted or unsubstituted alkyl group, and $R^2$ is a straight chain or branched halogenated alkyl or alkenyl group having 3 to 10 carbon atoms, X is a chlorine, bromine or iodine atom, and m is an integer of 1 to 12, provided that formula (2) represents a mixture of $L^1=L^2=L^3=L^4$=formula (a), $L^1=L^2=L^4$=formula (a) and $L^3$=formula (b), $L^1=L^4$=formula (a) and $L^2=L^3$=formula (b), $L^1=L^3$=formula (a) and $L^2=L^4$=formula (b), $L^1$=formula (a) and $L^2=L^3=L^4$=formula (b), and $L^1=L^2=L^3=L^4$=formula (b), and an optical recording medium comprising the phthalocyanine mixture.

10 Claims, No Drawings

PHTHALOCYANINE COMPOUNDS AND OPTICAL RECORDING MEDIA COMPRISING THEM

This application is a continuation of application Ser. No. 08/575,754, filed Dec. 20, 1995 now abandoned.

BACKGROUND OF THE INVENTION

1. Field of the Invention

The present invention relates to a dye useful as a near infrared light absorber which plays an important role in the optoelectronics-related field including novel recording materials for optical disks, information recording, display sensors, protective spectacles, etc. and it also relates to an optical recording medium, such as optical disks and optical cards, formed by incorporating the dye in the recording layer.

2. Description of the Related Art

Laser beams are employed for writing and reading in apparatuses for optical disks and optical cards. Particularly, as a recording system for optical recording media used in these apparatuses, the heat mode recording (thermal recording) through light to heat conversion is generally employed as a practical level. Hence, there have been proposed, as the recording layer, low melting metals, organic polymers, and in addition a variety of organic dyes that cause physical or chemical changes such as melting, vaporization, decomposition and sublimation. Since organic dyes having low melting or decomposition temperatures are especially preferred from the viewpoint of recording sensitivity, cyanine dyes, phthalocyanine dyes, naphthalocyanine dyes, azo dyes, etc. have primarily been developed for use as the recording layer.

For example, Japanese Patent Laid-Open No. 147286/1990 has proposed an optical recording medium incorporating a cyanine dye in the recording layer. However, the medium system was inferior in long-term shelf stability and light resistance and also insufficient in recording characteristics.

Optical recording media each incorporating an anthraquinone dye (e.g. Japanese Patent Laid-Open No. 224448/1983) or a naphthoquinone dye (e.g. Japanese Patent Laid-Open No. 224793/1983) in the recording layer have also been proposed, but both the media were inferior in long-term shelf stability and light resistance and also insufficient in recording characteristics, similarly to the medium of the cyanine dye.

In Japanese Patent Laid-Open Nos. 25886/1986, 43269/1990 (U.S. Pat. No. 4,960,538), 296885/1990, etc., optical recording media incorporating a naphthalocyanine dye in the recording layer have been proposed. The media system had an excellent light resistance but low reflectance of the recording layer and insufficient recording characteristics.

Further, techniques, in which phthalocyanine dyes, particularly alkoxy-substituted phthalocyanines are used in the recording layers of optical recording media, are widely known by Japanese Patent Laid-Open Nos. 154888/1986 (EP 186404), 197280/1986, 246091/1986, 39286/1987 (U.S. Pat. No. 4,769,307), 37991/1988, 39338/1988 and 502099/1990. Concerning the optical recording media in which the phthalocyanine dyes disclosed in these patent publications are used, it has hardly been mentioned that these media have sufficient performances in the sensitivity and recording characteristics. Japanese Patent Laid-Open No. 62878/1991 (U.S. Pat. No. 5,124,067) has improved these disadvantages, but even the improved product had a large error in the high speed recording and high density recoding by a laser beam and hence was still insufficient for practical use.

The application of an alkoxy-substituted naphthalocyanine, an aliphatic hydrocarbonoxy-substituted phthalocyanine and an alkenylthio-substituted phthalocyanine to optical recording media has been proposed in Japanese Patent Laid-Open Nos. 43269/1990 (U.S. Pat. No. 4,960,538) and 296885/1990, No. 37991/1988, and No. 39388/1988, respectively. However, no mention is made therein about the effects of the phthalocyanines on the sensitivity and recording characteristics of the media. In Japanese Patent Laid-Open Nos. 55769/1990 and 279448/1994, a technique is disclosed for the production of a low-symmetric, soluble phthalocyanine from two kinds of phthalonitrile derivatives. However, nothing is mentioned about its application to optical recording media.

Further, there have been found no optical recording media comprising other known dyes, which exhibit sufficient performances in the recording characteristics.

Since a laser beam of 400 to 900 nm is used to write and read signals in and from optical recording media, it is important to control the absorption coefficient and refractive index of a recording material in the vicinity of the oscillation wavelength of the laser used and to form pits with a good precision during writing. These conditions are particularly important in the high speed recording and high density recording having been recently desired. Therefore, it becomes necessary to develop a dye for optical recording media which has a high structural stability and a high refractive index, an excellent decomposition characteristics and a high sensitivity to a light in the vicinity of the oscillation wavelength of the laser. However, dyes for optical recording media having been developed to date were defective in the sensitivity (C/N ratio, optimum recording power) and recording characteristics (jitter, deviation) particularly in the high speed recording and high density recording.

SUMMARY OF THE INVENTION

An object of the present invention is to improve the above-described defects and prepare a novel phthalocyanine compound capable of offering optical recording media having a high sensitivity and excellent in the recording characteristics and durability.

Another object of the present invention is to provide a near infrared light-absorbing dye comprising a mixture containing the novel phthalocyanine compounds.

In the present invention, it is a further object to provide a process for preparing the near infrared light-absorbing dye, and it is a still further object to provide an optical recording medium containing the near infrared light-absorbing dye in the recording layer.

The present inventors have intensively reserched with the intention of achieving the above-mentioned objects, and finally, the present invention has now been completed. That is, the present invention provides a phthalocyanine compound represented by the following formula (1):

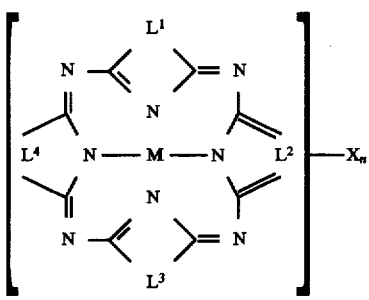

(1)

wherein in formula (1), M is two hydrogen atoms, a divalent metallic atom, a trivalent monosubstituted metallic atom, a tetravalent disubstituted metallic atom or an oxymetal atom, $L^1$, $L^2$, $L^3$ and $L^4$ are each independently formula (a) or (b):

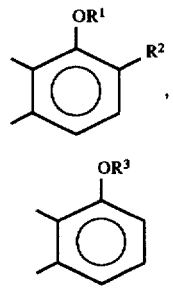

(a)

(b)

wherein in formula (a) or (b), $R^1$ and $R^3$ are each a substituted or unsubstituted alkyl group, and $R^2$ is a straight chain or branched halogenated alkyl or alkenyl group having 3 to 10 carbon atoms, X is a chlorine, bromine or iodine atom and n is an integer of 1 to 11, provided that at least one of $L^1$, $L^2$, $L^3$ and $L^4$ is formula (a), but all of $L^1$ to $L^4$ are not formula (a) at the same time.

Further, the present invention provides a near infrared light-absorbing dye comprising a phthalocyanine mixture represented by the following formula (2):

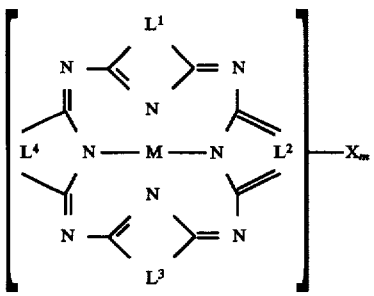

(2)

wherein in formula (2), M is two hydrogen atoms, a divalent metallic atom, a trivalent monosubstituted metallic atom, a tetravalent disubstituted metallic atom or an oxymetal atom, $L^1$, $L^2$, $L^3$ and $L^4$ are each independently formula (a) or (b):

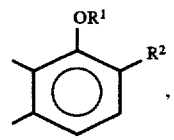

(a)

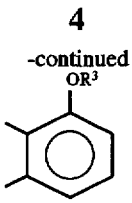

(b)

wherein in formula (a) or (b), $R^1$ and $R^3$ are each a substituted or unsubstituted alkyl group, and $R^2$ is a straight chain or branched halogenated alkyl or alkenyl group having 3 to 10 carbon atoms, X is a chlorine, bromine or iodine atom, and m is an integer of 1 to 12, provided that formula (2) denotes a mixture of $L^1=L^2=L^3=L^4$=formula (a), $L^1=L^2=L^4$=formula (a) and $L^3$=formula (b), $L^1=L^4$=formula (a) and $L^2=L^3$=formula (b), $L^1=L^3$=formula (a) and $L^2=L^4$=formula (b), $L^2=L^3=L^4$= formula (b) and $L^1$=formula (a), and $L^1=L^2=L^3=L^4$=formula (b).

Further, the present invention relates to an optical recording medium comprising the above-described near infrared light-absorbing dye and particularly to an optical recording medium having a structure in which a recording layer containing the near infrared light-absorbing dye of formula (2), a reflective layer made of gold or aluminum and a protective layer are laminated in this order on a substrate.

The phthalocyanine compound of the present invention has a sharp absorption at 650 to 900 nm, a high molecular absorptivity coefficient and an excellent long-term stability and light resistance, so that it is suitable for use as the recording material for optical recording media (optical disks, optical cards, etc.) using a semiconductor laser.

The dye of the present invention is a mixed system of low-symmetric phthalocyanine compounds. Therefore, the phthalocyanines are liable to have strains in the aza bonds and hence have improved decomposition characteristics upon laser irradiation, so that the decomposition and melting of the dye are controlled during recording to form pits with a high precision, and the damage to the resinous substrate of the recording medium is reduced due to the reduction of the amount of heat generated by the decomposition in a recording medium having a reflective layer, the dye contributes to improving the adhesion between the recording layer and a metallic layer, that is the reflective layer. Further, in optical recording media incorporating the dye therein, it becomes possible to write correctly signals during optical recording, thus effectively improving the sensitivity and recording characteristics of the media.

DETAILED DESCRIPTION OF THE PREFERRED EMBODIMENTS

The reason why the dye of the present invention is suitable for use as the recording material for optical recording media (optical disks, optical cards, etc.) is that the use of a mixed system of low-symmetric phthalocyanine compounds causes the phthalocyanines to be liable to have strains in the aza bonds and to have improved decomposition characteristics upon laser irradiation, thus contributing to the improvement of the sensitivity during recording and effectively reducing the error of the signals formed. In other words, it becomes possible by using the mixed system to control the melting and decomposition of the dye during optical recording, to reduce the damage to the substrate of the recording medium and to improve the adhesion between a reflective layer and the recording layer in a medium having the reflective layer.

Preferred embodiments of the present invention will be described in detail hereinbelow.

Illustrative examples of the substituted or unsubstituted alkyl groups represented by $R^1$ and $R^3$ in formulae (1) and (2) include hydrocarbon groups such as a methyl group, ethyl group, n-propyl group, iso-propyl group, n-butyl group, iso-butyl group, sec-butyl group, t-butyl group, n-pentyl group, iso-pentyl group, neopentyl group, 1,2-dimethylpropyl group, n-hexyl group, cyclohexyl group, 1,3-dimethylbutyl group, 1-iso-propylpropyl group, 1,2-dimethylbutyl group, n-heptyl group, 1,4-dimethylpentyl group, 2-methyl-1-iso-propylpropyl group, 1-ethyl-3-methylbutyl group, n-octyl group, 2-ethylhexyl group, 3-methyl-1-iso-propylbutyl group, 2-methyl-1-iso-propylbutyl group, 1-t-butyl-2-methylpropyl group and n-nonyl group; alkoxyalkyl groups such as a methoxymethyl group, methoxyethyl group, ethoxyethyl group, propoxyethyl group, butoxyethyl group, methoxyethoxyethyl group, ethoxyethoxyethyl group, dimethoxymethyl group, diethoxymethyl group, dimethoxyethyl group and diethoxyethyl group; and halogenated alkyl groups such as a chloromethyl group, 2,2,2-trichloroethyl group, trifluoromethyl group and 1,1,1,3,3,3-hexafluoro-2-propyl group.

Above all, the preferable alkyl group is an alkyl group having a total of 2 to 4 of the secondary and tertiary carbon atoms, including particularly a 1,2-dimethylpropyl group, 1,3-dimethylbutyl group, 1,2-dimethylbutyl group, 1-iso-propylpropyl group, 1,4-dimethylpentyl group, 2-methyl-1-iso-propylpropyl group, 1-ethyl-3-methylbutyl group, 3-methyl-1-iso-propylbutyl group, 2-methyl-1-iso-propylbutyl group and 1-t-butyl-2-methylpropyl group.

Illustrative examples of the straight chain or branched halogenated alkyl group having 3 to 10 carbon atoms represented by $R^2$ in formulae (1) and (2) include a 1,2-dichloropropyl group, 1,2-dibromopropyl group, 1,2-diiodopropyl group, 2,3-dichloropropyl group, 2,3-dibromopropyl group, 2,3-diiodopropyl group, 1-chloropropyl group, 1-bromopropyl group, 1-iodopropyl group, 2-chloropropyl group, 2-bromopropyl group, 2-iodopropyl group, 3-chloropropyl group, 3-bromopropyl group, 3-iodopropyl group, 1,2-dichloro-1-methylpropyl group, 1,2-dibromo-1-methylpropyl group, 1,2-diiodo-1-methylpropyl group, 2,3-dichloro-1-methylpropyl group, 2,3-dibromo-1-methylpropyl group, 2,3-diiodo-1-methylpropyl group, 1-chloro-1-methylpropyl group, 1-bromo-1-methylpropyl group, 1-iodo-1-methylpropyl group, 2-chloro-1-methylpropyl group, 2-bromo-1-methylpropyl group, 2-iodo-1-methylpropyl group, 3-chloro-1-methylpropyl group, 3-bromo-1-methylpropyl group, 3-iodo-1-methylpropyl group, 1,2-dichloro-1-ethylpropyl group, 1,2-dibromo-1-ethylpropyl group, 1,2-diiodo-1-ethylpropyl group, 2,3-dichloro-1-ethylpropyl group, 2,3-dibromo-1-ethylpropyl group, 2,3-diiodo-1-ethylpropyl group, 1-chloro-1-ethylpropyl group, 1-bromo-1-ethylpropyl group, 1-iodo-1-ethylpropyl group, 2-chloro-1-ethylpropyl group, 2-bromo-1-ethylpropyl group, 2-iodo-1-ethylpropyl group, 3-chloro-1-ethylpropyl group, 3-bromo-1-ethylpropyl group, 3-iodo-1-ethylpropyl group, 1,2-dichloro-1-propylpropyl group, 1,2-dibromo-1-propylpropyl group, 1,2-diiodo-1-propylpropyl group, 2,3-dichloro-1-propylpropyl group, 2,3-dibromo-1-propylpropyl group, 2,3-diiodo-1-propylpropyl group, 1-chloro-1-propylpropyl group, 1-bromo-1-propylpropyl group, 1-iodo-1-propylpropyl group, 2-chloro-1-propylpropyl group, 2-bromo-1-propylpropyl group, 2-iodo-1-propylpropyl group, 3-chloro-1-propylpropyl group, 3-bromo-1-propylpropyl group, 3-iodo-1-propylpropyl group, 2,3-dichloro-1,1-dimethylpropyl group, 2,3-dibromo-1,1-dimethylpropyl group, 2,3-diiodo-1,1-dimethylpropyl group, 2-chloro-1,1-dimethylpropyl group, 2-bromo-1,1-dimethylpropyl group, 2-iodo-1,1-dimethylpropyl group, 3-chloro-1,1-dimethylpropyl group, 3-bromo-1,1-dimethylpropyl group, 3-iodo-1,1-dimethylpropyl group, 1,2-dichlorobutyl group, 1,2-dibromobutyl group, 1,2-diiodobutyl group, 2,3-dichlorobutyl group, 2,3-dibromobutyl group, 2,3-diiodobutyl group, 1-chlorobutyl group, 1-bromobutyl group, 1-iodobutyl group, 2-chlorobutyl group, 2-bromobutyl group, 2-iodobutyl group, 3-chlorobutyl group, 3-bromobutyl group, 3-iodobutyl group, 1,2-dichloro-1-methylbutyl group, 1,2-dibromo-1-methylbutyl group, 1,2-diiodo-1-methylbutyl group, 2,3-dichloro-1-methylbutyl group, 2,3-dibromo-1-methylbutyl group, 2,3-diiodo-1-methylbutyl group, 1-chloro-1-methylbutyl group, 1-bromo-1-methylbutyl group, 1-iodo-1-methylbutyl group, 2-chloro-1-methylbutyl group, 2-bromo-1-methylbutyl group, 2-iodo-1-methylbutyl group, 3-chloro-1-methylbutyl group, 3-bromo-1-methylbutyl group, 3-iodo-1-methylbutyl group, 1,2-dichloro-2-methylbutyl group, 1,2-dibromo-2-methylbutyl group, 1,2-diiodo-2-methylbutyl group, 2,3-dichloro-2-methylbutyl group, 2,3-dibromo-2-methylbutyl group, 2,3-diiodo-2-methylbutyl group, 1-chloro-2-methylbutyl group, 1-bromo-2-methylbutyl group, 1-iodo-2-methylbutyl group, 2-chloro-2-methylbutyl group, 2-bromo-2-methylbutyl group, 2-iodo-2-methylbutyl group, 3-chloro-2-methylbutyl group, 3-bromo-2-methylbutyl group, 3-iodo-2-methylbutyl group, 1,2-dichloro-3-methylbutyl group, 1,2-dibromo-3-methylbutyl group, 1,2-diiodo-3-methylbutyl group, 2,3-dichloro-3-methylbutyl group, 2,3-dibromo-3-methylbutyl group, 2,3-diiodo-3-methylbutyl group, 1-chloro-3-methylbutyl group, 1-bromo-3-methylbutyl group, 1-iodo-3-methylbutyl group, 2-chloro-3-methylbutyl group, 2-bromo-3-methylbutyl group, 2-iodo-3-methylbutyl group, 3-chloro-3-methylbutyl group, 3-bromo-3-methylbutyl group, 3-iodo-3-methylbutyl group, 1,2-dichloro-2,3-dimethylbutyl group, 1,2-dibromo-2,3-dimethylbutyl group, 1,2-diiodo-2,3-dimethylbutyl group, 2,3-dichloro-2,3-dimethylbutyl group, 2,3-dibromo-2,3-dimethylbutyl group, 2,3-diiodo-2,3-dimethylbutyl group, 1-chloro-2,3-dimethylbutyl group, 1-bromo-2,3-dimethylbutyl group, 1-iodo-2,3-dimethylbutyl group, 2-chloro-2,3-dimethylbutyl group, 2-bromo-2,3-dimethylbutyl group, 2-iodo-2,3-dimethylbutyl group, 3-chloro-2,3-dimethylbutyl group, 3-bromo-2,3-dimethylbutyl group, 3-iodo-2,3-dimethylbutyl group, 2,3-dichloro-1,1-dimethylbutyl group, 2,3-dibromo-1,1-dimethylbutyl group, 2,3-diiodo-1,1-dimethylbutyl group, 2-chloro-1,1-dimethylbutyl group, 2-bromo-1,1-dimethylbutyl group, 2-iodo-1,1-dimethylbutyl group, 3-chloro-1,1-dimethylbutyl group, 3-bromo-1,1-dimethylbutyl group, 3-iodo-1,1-dimethylbutyl group, 1,2-dichloro-1-ethyl-2-methylbutyl group, 1,2-dibromo-1-ethyl-2-methylbutyl group, 1,2-diiodo-1-ethyl-2-methylbutyl group, 2,3-dichloro-1-ethyl-2-methylbutyl group, 2,3-dibromo-1-ethyl-2-methylbutyl group, 2,3-diiodo-1-ethyl-2-methylbutyl group, 1-chloro-1-ethyl-2-methylbutyl group, 1-bromo-1-ethyl-2-methylbutyl group, 1-iodo-1-ethyl-2-methylbutyl group, 2-chloro-1-ethyl-2-methylbutyl group, 2-bromo-1-ethyl-2-methylbutyl group, 2-iodo-1-ethyl-2-methylbutyl group, 3-chloro-1-ethyl-2-methylbutyl group, 3-bromo-1-ethyl-2-methylbutyl group, 3-iodo-1-ethyl-2-methylbutyl group, 1,2-dichloropentyl group, 1,2-dibromopentyl group, 1,2-diiodopentyl group, 2,3-dichloropentyl group, 2,3-dibromopentyl group, 2,3-diiodopentyl group, 1-chloropentyl group, 1-bromopentyl group, 1-iodopentyl group, 2-chloropentyl group, 2-bromopentyl group, 2-iodopentyl group, 3-chloropentyl group, 3-bromopentyl group, 3-iodopentyl group, 1,2-dichloro-1-methylpentyl group, 1,2-dibromo-1-methylpentyl group, 1,2-diiodo-1-methylpentyl group, 2,3-dichloro-1-methylpentyl group, 2,3-dibromo-1-methylpentyl group, 2,3-diiodo-1-methylpentyl group, 1-chloro-1-methylpentyl group, 1-bromo-1-methylpentyl group, 1-iodo-1-methylpentyl group, 2-chloro-1-methylpentyl group, 2-bromo-1-methylpentyl group, 2-iodo-1-methylpentyl group, 3-chloro-1-methylpentyl group, 3-bromo-1-methylpentyl group, 3-iodo-1-methylpentyl group, 1,2-dichloro-2-methylpentyl group, 1,2-dibromo-2-methylpentyl group, 1,2-diiodo-2-methylpentyl group, 2,3-dichloro-2-methylpentyl group, 2,3-dibromo-2-methylpentyl group, 2,3-diiodo-2-methylpentyl group, 1-chloro-2-methylpentyl group, 1-bromo-2-methylpentyl group, 1-iodo-2-methylpentyl group, 2-chloro-2-methylpentyl group, 2-bromo-2-methylpentyl group, 2-iodo-2-methylpentyl group, 3-chloro-2-methylpentyl group, 3-bromo-2-methylpentyl group, 3-iodo-2-methylpentyl group, 1,2-dichloro-3-methylpentyl group, 1,2-dibromo-3-methylpentyl group, 1,2-diiodo-3-methylpentyl group, 2,3-dichloro-3-methylpentyl group, 2,3-dibromo-3-methylpentyl group, 2,3-diiodo-3-methylpentyl group, 1-chloro-3-methylpentyl group, 1-bromo-3-methylpentyl group, 1-iodo-3-methylpentyl group, 2-chloro-3-methylpentyl group, 2-bromo-3-methylpentyl group, 2-iodo-3-methylpentyl group, 3-chloro-3-methylpentyl group, 3-bromo-3-methylpentyl group, 3-iodo-3-methylpentyl group, 1,2-dichloro-4-methylpentyl group, 1,2-dibromo-4-methylpentyl group, 1,2-diiodo-4-methylpentyl group, 2,3-dichloro-4-methylpentyl group, 2,3-dibromo-4-methylpentyl group, 2,3-diiodo-4-methylpentyl group, 1-chloro-4-methylpentyl group, 1-bromo-4-methylpentyl group, 1-iodo-4-methylpentyl group, 2-chloro-4-methylpentyl group, 2-bromo-4-methylpentyl group, 2-iodo-4-methylpentyl group, 3-chloro-4-methylpentyl group, 3-bromo-4-methylpentyl group, 3-iodo-4-methylpentyl group, 1,2-dichloro-2,4-dimethylpentyl group, 1,2-dibromo-2,4-dimethylpentyl group, 1,2-diiodo-2,4-dimethylpentyl group, 2,3-dichloro-2,4-dimethylpentyl group, 2,3-dibromo-2,4-dimethylpentyl group, 2,3-diiodo-2,4-dimethylpentyl group, 1-chloro-2,4-dimethylpentyl group, 1-bromo-2,4-dimethylpentyl group, 1-iodo-2,4-dimethylpentyl group, 2-chloro-2,4-dimethylpentyl group, 2-bromo-2,4-dimethylpentyl group, 2-iodo-2,4-dimethylpentyl group, 3-chloro-2,4-dimethylpentyl group, 3-bromo-2,4-dimethylpentyl group, 3-iodo-2,4-dimethylpentyl group, 1,2-dichloro-2,4-dimethylpentyl group, 1,2-dibromo-2,4-dimethylpentyl group, 1,2-diiodo-2,4-dimethylpentyl group, 2,3-dichloro-1,4-dimethylpentyl group, 2,3-dibromo-1,4-dimethylpentyl group, 2,3-diiodo-1,4-dimethylpentyl group, 1-chloro-1,4-dimethylpentyl group, 1-bromo-1,4-dimethylpentyl group, 1-iodo-1,4-dimethylpentyl group, 2-chloro-1,4-dimethylpentyl group, 2-bromo-1,4-dimethylpentyl group, 2-iodo-1,4-dimethylpentyl group, 3-chloro-1,4-dimethylpentyl group, 3-bromo-1,4-dimethylpentyl group, 3-iodo-1,4-dimethylpentyl group, 1,2-dichloro-1-ethyl-2-methylpentyl group, 1,2-dibromo-1-ethyl-2-methylpentyl group, 1,2-diiodo-1-ethyl-2-methylpentyl group, 2,3-dichloro-1-ethyl-2-methylpentyl group, 2,3-dibromo-1-ethyl-2-methylpentyl group, 2,3-diiodo-1-ethyl-2-methylpentyl group, 1-chloro-1-ethyl-2-methylpentyl group, 1-bromo-1-ethyl-2-methylpentyl group, 1-iodo-1-ethyl-2-methylpentyl group, 2-chloro-1-ethyl-2-methylpentyl group, 2-bromo-1-ethyl-2-methylpentyl group, 2-iodo-1-ethyl-2-methylpentyl group, 3-chloro-1-ethyl-2-methylpentyl group, 3-bromo-1-ethyl-2-methylpentyl group, 3-iodo-1-ethyl-2-methylpentyl group, 1,2-dichloro-1-ethyl-3-methylpentyl group, 1,2-dibromo-1-ethyl-3-methylpentyl group, 1,2-diiodo-1-ethyl-3-methylpentyl group, 2,3-dichloro-1-ethyl-3-methylpentyl group, 2,3-dibromo-1-ethyl-3-methylpentyl group, 2,3-diiodo-1-ethyl-3-methylpentyl group, 1-chloro-1-ethyl-3-methylpentyl group, 1-bromo-1-ethyl-3-methylpentyl group, 3-iodo-1-ethyl-3-methylpentyl group, 2-chloro-1-ethyl-3-methylpentyl group, 2-bromo-1-ethyl-3-methylpentyl group, 2-iodo-1-ethyl-3-methylpentyl group, 3-chloro-1-ethyl-3-methylpentyl group, 3-bromo-1-ethyl-3-methylpentyl group, 3-iodo-1-ethyl-3-methylpentyl group, 1,2-dichloro-1-ethyl-4-methylpentyl group, 1,2-dibromo-1-ethyl-4-methylpentyl group, 1,2-diiodo-1-ethyl-4-methylpentyl group, 2,3-dichloro-1-ethyl-4-methylpentyl group, 2,3-dibromo-1-ethyl-4-methylpentyl group, 2,3-diiodo-1-ethyl-4-methylpentyl group, 1-chloro-1-ethyl-4-methylpentyl group, 1-bromo-1-ethyl-4-methylpentyl group, 3-iodo-1-ethyl-4-methylpentyl group, 2-chloro-1-ethyl-4-methylpentyl group, 2-bromo-1-ethyl-4-methylpentyl group, 2-iodo-1-ethyl-4-methylpentyl group, 3-chloro-1-ethyl-4-methylpentyl group, 3-bromo-1-ethyl-4-methylpentyl group, 3-iodo-1-ethyl-4-methylpentyl group, 1,2-dichlorohexyl group, 1,2-dibromohexyl group, 1,2-diiodohexyl group, 2,3-dichlorohexyl group, 2,3-dibromohexyl group, 2,3-diiodohexyl group, 1-chlorohexyl group, 1-bromohexyl group, 1-iodohexyl group, 2-chlorohexyl group, 2-bromohexyl group, 2-iodohexyl group, 3-chlorohexyl group, 3-bromohexyl group, 3-iodohexyl group, 1,2-dichloro-1-methylhexyl group, 1,2-dibromo-1-methylhexyl group, 1,2-diiodo-1-methylhexyl group, 2,3-dichloro-1-methylhexyl group, 2,3-dibromo-1-methylhexyl group, 2,3-diiodo-1-methylhexyl group, 1-chloro-1-methylhexyl group, 1-bromo1-methylhexyl group, 1-iodo-1-methylhexyl group, 2-chloro-1-methylhexyl group, 2-bromo-1-methylhexyl group, 2-iodo-1-methylhexyl group, 3-chloro-1-methylhexyl group, 3-bromo-1-methylhexyl group, 3-iodo-1-methylhexyl group, 1,2-dichloro-3-methylhexyl group, 1,2-dibromo-3-methylhexyl group, 1,2-diiodo-3-methylhexyl group, 2,3-dichloro-3-methylhexyl group, 2,3-dibromo-3-methylhexyl group, 2,3-diiodo-3-methylhexyl group, 1-chloro-3-methylhexyl group, 1-bromo-3-methylhexyl group, 1-iodo-3-methylhexyl group, 2-chloro-3-methylhexyl group, 2-bromo-3-methylhexyl group, 2-iodo-3-methylhexyl group, 3-chloro-3-methylhexyl group, 3-bromo-3-methylhexyl group, 3-iodo-3-methylhexyl group, 1,2-dichloroheptyl group, 1,2-dibromoheptyl group, 1,2-diiodoheptyl group, 2,3-dichloroheptyl group, 2,3-dibromoheptyl group, 2,3-diiodoheptyl group, 1-chloroheptyl group, 1-bromoheptyl group, 1-iodoheptyl group, 2-chloroheptyl group, 2-bromoheptyl group, 2-iodoheptyl group, 3-chloroheptyl group, 3-bromoheptyl group, 3-iodoheptyl group, 1,2-dichloro-2-methylheptyl group, 1,2-dibromo-2-methylheptyl group, 1,2-diiodo-2-methylheptyl group, 2,3-dichloro-2-methylheptyl group, 2,3-dibromo-2-methylheptyl group, 2,3-diiodo-2-methylheptyl group, 1-chloro-2-methylheptyl group, 1-bromo-2-methylheptyl group, 1-iodo-2-methylheptyl group, 2-chloro-2-methylheptyl group, 2-bromo-2-methylheptyl group, 2-iodo-2-methylheptyl group, 3-chloro-2-methylheptyl group, 3-bromo-2-methylheptyl group, 3-iodo-2-methylheptyl group, 1,2-dichloro-3,4,4-trimethylheptyl group, 1,2-dibromo-3,4,4-trimethylheptyl group, 1,2-diiodo-3,4,4-trimethylheptyl group, 2,3-dichloro- 3,4,4-trimethylheptyl group, 2,3-dibromo-3,4,4-trimethylheptyl group, 2,3-diiodo-3,4,4-trimethylheptyl group, 1-chloro-3,4,4-trimethylheptyl group, 1-bromo-3,4,4-trimethylheptyl group, 1-iodo-3,4,4-trimethylheptyl group, 2-chloro-3,4,4-trimethylheptyl group, 2-bromo-3,4,4-trimethylheptyl group, 2-iodo-3,4,4-trimethylheptyl group, 3-chloro-3,4,4-trimethylheptyl group, 3-bromo-3,4,4-trimethylheptyl group, 3-iodo-3,4,4-trimethylheptyl group, 1,2-dichlorooctyl group, 1,2-dibromooctyl group, 1,2-diiodooctyl group, 2,3-dichlorooctyl group, 2,3-dibromooctyl group, 2,3-diiodooctyl group, 1-chlorooctyl group, 1-bromooctyl group, 1-iodooctyl group, 2-chlorooctyl group, 2-bromooctyl group, 2-iodooctyl group, 3-chlorooctyl group, 3-bromooctyl group, 3-iodooctyl group, 1,2-dibromononyl group, 1,2-diiodononyl group, 2,3-dichlorononyl group, 2,3-dibromononyl group, 2,3-diiodononyl group, 1-chlorononyl group, 1-bromononyl group, 1-iodononyl group, 2-chlorononyl group, 2-bromononyl group, 2-iodononyl group, 3-chlorononyl group, 3-bromononyl group, 3-iodononyl group, 1,2-dichlorodecanyl group, 1,2-dibromodecanyl group, 1,2-diiododecanyl group, 2,3-dichlorodecanyl group, 2,3-dibromodecanyl group, 2,3-diiododecanyl group, 1-chlorodecanyl group, 1-bromodecanyl group, 1-iododecanyl group, 2-chlorodecanyl group, 2-bromodecanyl group, 2-iododecanyl group, 3-chlorodecanyl group, 3-bromodecanyl group, 3-iododecanyl group, and the like.

Illustrative examples of the alkenyl group having 3 to 10 carbon atoms represented by $R^2$ in formulae (1) and (2) include alkenyl groups such as a propenyl group, 2-propenyl group, 1-methylpropenyl group, 1-methyl-2-propenyl group, 1-ethylpropenyl group, 1-ethyl-2-propenyl group, 1-propylpropenyl group, 1-propyl-2-propenyl group, 1,1-dimethyl-2-propenyl group, butenyl group, 2-butenyl group, 1-methyl-2-butenyl group, 1-methylbutenyl group, 2-methyl-2-butenyl group, 2-methylbutenyl group, 3-methyl-2-butenyl group, 3-methylbutenyl group, 2,3-dimethyl-2-butenyl group, 2,3-dimethylbutenyl group, 1,1-dimethyl-2-butenyl group, 1-ethyl-2-methyl-2-butenyl group, 1-ethyl-2-methylbutenyl group, pentenyl group, 2-pentenyl group, 1-methyl-2-pentenyl group, 1-methylpentenyl group, 2-methyl-2-pentenyl group, 2-methylpentenyl group, 3-methyl-2-pentenyl group, 3-methylpentenyl group, 4-methyl-2-pentenyl group, 4-methylpentenyl group, 2,4-dimethyl-2-pentenyl group, 2,4-dimethylpentenyl group, 1,4-dimethyl-2-pentenyl group, 1,4-dimethylpentenyl group, 1-ethyl-2-methyl-2-pentenyl group, 1-ethyl-2-methylpentenyl group, 2-hexenyl group, hexenyl group, 1-methyl-2-hexenyl group, 1-methylhexenyl group, 3-methyl-2-hexenyl group, 3-methylhexenyl group, 2-heptenyl group, heptenyl group, 2-methyl-2-heptenyl group, 2-methylheptenyl group, 3,4,4-trimethyl-2-heptenyl group, 3,4,4-trimethylheptenyl group, 2-octenyl group, octenyl group, 2-nonenyl group, nonenyl group, 2-decenyl group and decenyl group.

In formulae (1) and (2), examples of the divalent metal represented by M include Cu, Zn, Fe, Co, Ni, Ru, Rh, Pd, Pt, Mn, Sn, Mg, Pb, Hg, Cd, Ba, Ti, Be, Ca, etc.; examples of the monosubstituted trivalent metal include Al-F, Al-Cl, Al-Br, Al-I, Ga-F, Ga-Cl, Ga-Br, Ga-I, In-F, In-Cl, In-Br, In-I, Tl-F, Tl-Cl, Tl-Br, Tl-I, Al-C$_6$H$_5$, Al-C$_6$H$_4$(CH$_3$), In-C$_6$H$_5$, In-C$_6$H$_4$(CH$_3$), Mn(OH), Mn(OC$_6$H$_5$), Mn[OSi(CH$_3$)$_3$], Fe-Cl, Ru-Cl, etc.; examples of the disubstituted tetravalent metal include CrCl$_2$, SiF$_2$, SiCl$_2$, SiBr$_2$, SiI$_2$, SnF$_2$, SnCl$_2$, SnBr$_2$, ZrCl$_2$, GeF$_2$, GeCl$_2$, GeBr$_2$, GeI$_2$, TiF$_2$, TiCl$_2$, TiBr$_2$, Si(OH)$_2$, Sn(OH)$_2$, Ge(OH)$_2$, Zr(OH)$_2$, Mn(OH)$_2$, TiA$_2$, CrA$_2$, SiA$_2$, SnA$_2$, GeA$_2$ (in which A is an alkyl group, phenyl group or naphthyl group or a derivative thereof), Si(OA')$_2$, Sn(OA')$_2$, Ge(OA')$_2$, Ti(OA')$_2$, Cr(OA')$_2$ (in which A' is an alkyl group, phenyl group, naphthyl group, trialkylsilyl group or dialkylalkoxysilyl group or a derivative thereof), Si(SA")$_2$, Sn(SA")$_2$, and Ge(SA")$_2$ (in which A" is an alkyl group, phenyl group or naphthyl group or a derivative thereof); and examples of the oxymetal include VO, MnO, TiO, etc. Preferably, M is Pd, Cu, Ru, Pt, Ni, Co, Rh, Zn, Vo, TiO, Si(Y)$_2$, Sn(Y)$_2$, Ge(Y)$_2$ (wherein Y is a halogen atom, alkoxy group, aryloxy group, acyloxy group, hydroxy group, alkyl group, aryl group, alkylthio group, arylthio group, trialkylsilyl-oxy group, trialkyltinoxy or trialkylgermaniumoxy group). The particularly preferred M includes Cu, Ni, Co, Mg, Zn, Pd, Pt and VO.

To prepare the phthalocyanine compound represented by formulae (1) and (2) and the mixture, compounds of formulae (3) and (4):

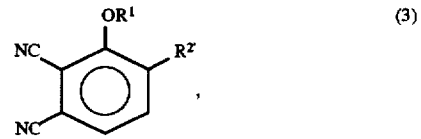

(3)

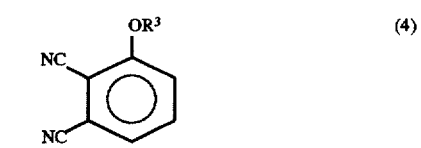

(4)

(wherein $R^1$ and $R^3$ have the same meanings as described above, and $R^{2'}$ is a straight chain or branched alkenyl group having 3 to 10 carbon atoms) or compounds of formulae (5) and (6), that are obtained by reacting ammonia with the compounds of formulae (3) and (4) in an alcohol in the presence of a catalyst of sodium methylate,

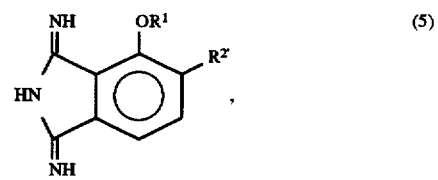

(5)

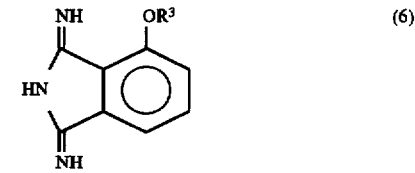

(6)

(wherein $R^1$, $R^3$ and $R^{2'}$ has the same meanings as described above) are reacted with each other in a solvent in a molar ratio of formula (3):formula (4)=formula (5):formula (6)= 1:1–15 in the presence or absence of a metal compound, followed by reaction with a halogenating agent. The reaction temperature is 100° to 300° C., preferably 135° to 220° C.

Examples of the alkenyl group represented by $R^{2'}$ are same as examples of the alkenyl group represented by $R^2$.

The amount of the solvent used is 1 to 100 times by weight, preferably 5 to 20 times by weight as much as that of the phthalonitrile or diiminoisoindoline.

The solvent is an alcohol or aromatic solvent with a boiling point of 135° C. or above, including, for example, n-amyl alcohol, n-hexanol, cyclohexanol, 2-methyl-1-pentanol, 1-heptanol, 2-heptanol, 1-octanol, 2-ethylhexanol, benzyl alcohol, ethylene glycol, propylene glycol, ethoxyethanol, propoxyethanol, butoxyethanol, chloronaphthalene, bromonaphthalene, trichlorobenzene, etc.

The metal compound used in the reaction embraces Al, Si, Ca, Ti, V, Fin, Fe, Co, Ni, Cu, Zn, Ge, Mo, Ru, Rh, Pd, In, Sn, Pt and the halides, carboxylic acid derivatives, sulfates, carbonyl compounds, oxides and complexes thereof. Preferably used are copper chloride, copper bromide, copper iodide, copper acetate, nickel chloride, nickel bromide, nickel acetate, palladium chloride, palladium bromide, palladium acetate, platinum chloride, platinum bromide, zinc chloride, zinc bromide and zinc acetate.

The amounts of the metal compound and the phthalonitrile or diiminoisoindoline are preferably 1:3 to 1:6 by mole.

Further, as the ring-forming reaction catalyst, it is advisable to add an organic base, for example, a strongly basic assistant such as 1,8-diazabicyclo[5.4.0]-7-undecene (DBU) and 1,5-diazabicyclo[4.3.0]-5-nonene (DBN). The amount of the base added is 0.1 to 10 moles, preferably 0.5 to 2 moles for each mole of the phthalonitrile or diiminoisoindoline.

Thus, there can be obtained a mixture of six kinds of phthalocyanine compounds represented by the following formula (7):

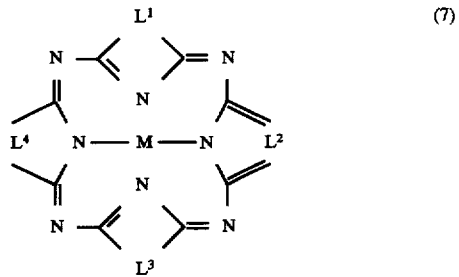

wherein in formula (7), M is two hydrogen atoms, a divalent metallic atom, a trivalent monosubstituted metallic atom, a tetravalent disubstituted metallic atom or an oxymetal atom, and $L^1$, $L^2$, $L^3$ and $L^4$ are each independently formula (a') or (b),

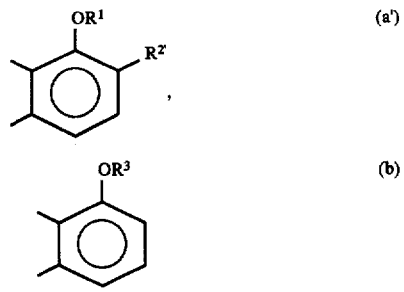

wherein in formula (a') or (b), $R^1$, $R^{2'}$ and $R^3$ have the same meanings as described above.

Namely, there is obtained a mixture of six compounds of formula (7):

1) $L^1=L^2=L^3=L^4$=formula (a'),
2) $L^1=L^2=L^4$=formula (a') and $L^3$=formula (b),
3) $L^1=L^4$=formula (a') and $L^2=L^3$=formula (b),
4) $L^1=L^3$=formula (a') and $L^2=L^4$=formula (b),
5) $L^2=L^3=L^4$=formula (b) and $L^1$=formula (a'), and
6) $L^1=L^2=L^3=L^4$=formula (b).

Regarding the proportions of their formation, when the molar ratio of the phthalonitrile or diiminoisoindoline represented by formula (4) or (6) is increased, fixing the molar amount of the phthalonitrile or diiminoisoindoline represented by formula (3) or (5) at 1, the proportions of the formation of the phthalocyanine compounds 1) to 6) are as follows:

| Compound | 1) | 2) | 3) | 4) | 5) | 6) |
|---|---|---|---|---|---|---|
| Mol ratio of formula (3):(4) (5):(6) | | | | | | |
| 1:1 | 6.25 | 25 | 25 | 12.5 | 25 | 6.25 |
| 1:3 | 0.3 | 4.7 | 14.1 | 7.0 | 42.2 | 31.6 |
| 1:15 | 0 | 0.1 | 1.4 | 0.7 | 20.6 | 77.2 |

As the halogenating agent to be used in the halogenation reaction, a compound represented by the following formula (8):

$$X—Y \qquad (8)$$

wherein X is a halogen atom and Y is the residue of the halogenating agent, may be used. The halogen atom may include F, Cl, Br and I. A preferred halogen atom is Br. The residue of the halogenating agent may embrace Cl, Br, I, $SO_2Cl$, SOCl, $FeCl_2$, $PCl_4$, $POCl_2$, CuBr, quaternary ammonium, etc.

Specifically, the halogenating agent includes chlorine, bromine, iodine, sulfuryl chloride, thionyl chloride, antimony chloride, $ICl_3$, $FeCl_3$, phosphorus pentachloride, phosphorus oxychloride, t-butyl hypochlorite, N-chlorosuccinic imide, copper (II) bromide, quaternary ammonium bromide, N-bromosuccinic imide, iodine monochloride, quaternary ammonium iodide, potassium triiodide, etc. Among these compounds, bromine is particularly preferred. The amount of the halogenating agent used is properly 1 to 12 times by mole depending on the desired amount of the halogen introduced.

The solvent is one capable of dissolving the phthalocyanine compound and the mixture, and preferably includes saturated hydrocarbons, ethers, halogenated hydrocarbons, etc. Specifically, it includes n-hexane, n-pentane, n-octane, cyclohexane, methylcyclohexane, ethylcyclohexane, tetrahydrofuran, n-butyl ether, n-propyl ether, isopropyl ether, carbon tetrachloride, chloroform, dichloromethane, 1,1,1-trichloroethane, 1,1,2-trichloroethane, 1,1,2,2-tetrachloroethane, etc.

The amount of the solvent used is 1 to 100 times by weight, preferably 5 to 20 times by weight as much as that of the phthalocyanine compound or the mixture.

The reaction temperature is 20° to 90° C., preferably 40° to 70° C.

The thus prepared phthalocyanine compound is a mixture of 6 or more isomers or compounds having different contents of a halogen atom. When this mixture is used without separation to prepare an optical recording medium, the medium which can solve the above-mentioned problems can be obtained. Even if the composition ratio of the mixture is varied, the performance of the optical recording medium does not deteriorate.

To prepare an optical recording medium by the use of the phthalocyanine dye of the present invention, a transparent substrate is coated or vapor-deposited with the phthalocyanine dye in one or two layers. In the coating method, the substrate is coated with a solution, formed by dissolving in a solvent 20% by weight or less, preferably 0% of a binder resin and 0.05 to 20% by weight, preferably 0.5 to 20% by weight of the phthalocyanine dye of the present invention, by means of a spin coater. Further, in the deposition method, the phthalocyanine dye is deposited on the substrate at $10^{-5}$ to $10^{-7}$ Torr and 100° to 300° C.

The substrate may be made of an optically transparent resin. For example, acrylic resins, polyethylene resins, vinyl chloride resins, vinylidene chloride resins, polycarbonate resins, polyolefin copolymer resins, vinyl chloride copolymer resins, vinylidene chloride copolymer resins and styrene copolymer resins may be mentioned. Further, the substrate may be surface-treaded with a thermosetting resin or ultraviolet-curing resin.

In the preparation of the optical recording medium (optical disk, optical card, etc.), it is preferable to use a polyacrylate or polycarbonate substrate and coat the substrate by a spin coating method from the viewpoints of cost and user's handleability.

In view of the solvent resistance of the substrate, the solvent used for the spin coating suitably includes halogenated hydrocarbons (e.g. dichloromethane, chloroform, carbon tetrachloride, tetrachloroethylene, dichlorodifluoroethane, etc.), ethers (e.g. tetrahydrofuran, diethyl ether, dipropyl ether, dibutyl ether, dioxane, etc.), alcohols (e.g. methanol, ethanol, propanol, etc.), Cellosolves (e.g. methyl Cellosolve, ethyl Cellosolve, etc.), hydrocarbons (e.g. hexane, cyclohexane, ethylcyclohexane, cyclooctane, dimethylcyclohexane, octane, benzene, toluene, xylene, etc.), and mixed solvents thereof.

To fabricate the recording medium, a recording layer is covered with a substrate as described above, or two substrates provided with recording layers are put together with the recording layers facing each other and an air gap inbetween. Alternatively, a reflective layer (aluminum or gold) is arranged on a recording layer, and a protective layer made of a thermosetting or photosetting resin is laminated thereon. Inorganic compounds such as $Al_2O_3$, $SiO_2$, SiO and $SnO_2$ may also be used as the protective layer.

Now, the present invention will be described in detail with reference to the following examples, but the scope of the present invention should not be limited only to these examples.

EXAMPLE 1

A mixture consisting of 10 g (30.8 mmol) of a phthalonitrile derivative given by the following formula (3-1), 22.4 g (92.5 mmol) of a phthalonitrile derivative given by the following formula (4-1), 18.7 g (123 mmol) of DBU and 300 ml of n-amyl alcohol was heated to 95° C. in a nitrogen atmosphere. Then, 6.6 g (37 mmol) of palladium chloride was added thereto at the same temperature, followed by reaction at 100° to 105° C. for 15 hours. After completion of the reaction, the solvent was distilled off and 1 liter of methanol was added to the resultant reaction mixture, the precipitate so formed being separated by filtration. After drying, the precipitate was purified by column chromatography (silica gel 1.4 kg, solvent=toluene:hexane=4:1) to obtain a green mixed phthalocyanine. The results of its maximum absorption wavelength ($\lambda_{max}$) and gram extinction coefficient ($\epsilon_g$) are as follows:

$\lambda_{max}$=690 nm, $\epsilon_g$=2.2×10$^5$ cm$^2$/g (solvent=toluene)

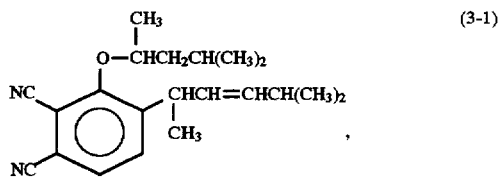
(3-1)

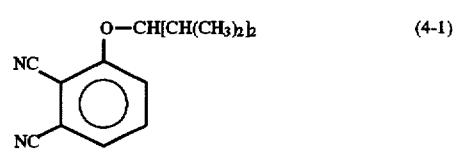
(4-1)

Then, a mixture consisting of 7.8 g of the green mixed phthalocyanine obtained above, 70 ml of water and 100 ml of 1,1,2-trichloroethane was heated to 45° to 50° C. Subsequently, a mixed solution comprising 6.5 g (36 mmol) of bromine and 10 ml of 1,1,2-trichloroethane was added thereto dropwise in 50 minutes at the same temperature, followed by reaction for 3 hours at the same temperature. After completion of the reaction, 20 g of a 10% aqueous sodium hydrogen sulfite solution was added to the reaction mixture, which was stirred for 20 minutes. After neutralization with a 10% aqueous sodium hydroxide solution, the contents were separated into two phases, and the organic phase was poured into a 90% aqueous methanol solution, the precipitate so formed being separated by filtration. After drying, the precipitate was purified by column chromatography (silica gel 1.0 kg, solvent=toluene:hexane=1:1) to obtain 9.0 g of a dark green, brominated mixed phthalocyanine. The results of the maximum absorption wavelength ($\lambda_{max}$) and gram extinction coefficient ($\epsilon_g$) are as follows:

$\lambda_{max}$=713.5 nm, $\epsilon_g$=1.3×10$^5$ cm$^2$/g (solvent=toluene).

An n-octane solution of the above-described brominated mixed phthalocyanine (10 g/l) was applied by spin coating at 500 to 1,000 rpm onto a polycarbonate substrate for CD-R having an outer diameter of 120 mm and a thickness of 1.2 mm and provided with a spiral groove (pitch 1.6 µm, groove width 0.6 µm, groove depth 0.18 µm) to form a film. Then, 30 nm of gold was deposited thereon by sputtering to form a reflective layer, which was then overcoated with a photosetting polyacrylic resin. Subsequently, the resin was photoset to form a protective layer, so that a CD-R type medium was prepared. The reflectance of the medium was 71% (775–790 nm) and hence an EFM signal could be written into the medium at a linear velocity of 1.3 m/sec with a power of 5.5 mW by using a semiconductor laser of 780 nm. The error rate at that time was less than 10, and no change was observed in the medium in a durability test at 63° C. for 200 hours by a carbon-arc lamp.

EXAMPLE 2

A mixture comprising 11.3 g of the green mixed phthalocyanine obtained in Example 1, 70 ml of water and 100 ml of 1,1,2-trichloroethane was heated to 45° to 50° C. Then, a mixed solution consisting of 19.5 g (84 mmol) of sulfuryl chloride and 10 ml of 1,1,2-trichloethane was added thereto dropwise in 50 minutes at the same temperature, followed by reaction for 2 hours at the same temperature. After completion of the reaction, the reaction mixture was neutralized with 180 g of a 10% aqueous sodium hydroxide solution, to which 1.5 liters of toluene was then added for extraction. The resultant mixture was separated into two phases, and the organic phase was washed with 400 ml of water twice. Then, the solvent was distilled off the organic phase, and the residue was dried and purified by column chromatography (silica gel 1.0 kg, solvent=toluene:hexane=1:1) to obtain 11 g of a dark green, chlorinated mixed phthalocyanine. The results of its maximum absorption wavelength ($\lambda_{max}$) and gram extinction coefficient ($\epsilon_g$) are as follows:

$\lambda_{max}$=704.0 nm, $\epsilon_g$=1.4×10$^5$ cm$^2$/g (solvent=toluene)

A dibutyl ether solution of the above-described chlorinated mixed phthalocyanine (10 g/l) was applied on a polycarbonate substrate for CD-R by a spin coater in the same manner as in Example 1. Gold was deposited thereon by sputtering and a UV-curing resin was applied further thereon to form a protective layer, so that a CD-R type medium was prepared. When a record was made in the medium by a semiconductor laser of 780 nm, a CN ratio of 60 dB was obtained with a power of 7.0 mW. No change was observed in the medium when it was reproduced a million times by a reproduction light of 0.5 mW. Further, the medium had no trouble in the recording and reproduction even after a lapse of 1,000 hours under the conditions of 80° C./85% R.H.

EXAMPLE 3

A mixed solution of 18.7 g (123 mmol) of DBU and 300 ml of n-octyl alcohol was heated to 170° C. in a nitrogen atmosphere. Then, a mixture consisting of 8.8 g (30.8 mmol) of a diiminoisoindoline derivative given by the following formula (5-1), 24.0 g (92.5 mmol) of a diiminoisoindoline derivative given by the following formula (6-1) and 6.6 g (37 mmol) of palladium chloride was added thereto at the same temperature, followed by reaction at 180° to 190° C. for 4 hours. After completion of the reaction, 1 liter of methanol was added to the reaction mixture and the precipitate so formed was separated by filtration. After drying, the precipitate was purified by column chromatography (silica gel 1.4 kg, solvent=toluene:hexane=4:1) to obtain 22 g of a green mixed phthalocyanine. The results of its maximum absorption wavelength ($\lambda_{max}$) and gram extinction coefficient ($\epsilon_g$) are as follows:

$\lambda_{max}$=691 nm, $\epsilon_g$=2.1×10$^5$ cm$^2$/g (solvent:toluene)

Then, a mixture consisting of 7.8 g of the green mixed phthalocyanine obtained as described above, 70 ml of water and 100 ml of 1,1,2-trichloroethane was heated to 45° to 50° C. Subsequently, a mixed solution comprising 6.5 g (36 mmol) of bromine and 10 ml of 1,1,2-trichloroethane was added thereto dropwise in 50 minutes at the same temperature, followed by reaction for 3 hours at the same temperature. After completion of the reaction, 20 g of a 10% aqueous sodium hydrogen sulfite solution were add to the reaction mixture, and the resultant mixture was stirred for 20 minutes. After neutralizing with a 10% aqueous sodium hydroxide solution, the mixture was separated into two phases and the organic phase was discharged into a 90% methanol solution, the precipitate so formed being separated by filtration. After drying, the precipitate was purified by column chromatography (silica gel 1.0 kg, solvent=toluene:hexane=1:1) to obtain 10 g of a dark green, brominated mixed phthalocyanine. The results of its maximum absorption wavelength ($\lambda_{max}$) and gram extinction coefficient ($\epsilon_g$) are as follows:

$\lambda_{max}$=713.0 nm, $\epsilon_g$=1.4×10$^5$ cm$^2$/g (solvent:toluene)

Ten grams of the above-described brominated mixed phthalocyanine were dissolved in 500 ml of a 3:1 (volume ratio) mixed solvent of dibutyl ether and diisopropyl ether, and the solution was applied on a polycarbonate substrate for CD-R by a spin coater to form a film. Gold was deposited on the film by sputtering, and then a UV-curing resin was applied thereon to form a protective layer. Thus, a CD-R type medium was prepared. The reflectance of the medium was 73% (775–790 nm), and hence an EFM signal could be written in the medium at a linear velocity of 1.3 m/sec with a power of 6.0 mW by means of a semiconductor laser of 780 nm. The error rate at that time was less than 10.

EXAMPLE 4

A mixture comprising 11.3 g of the green mixed phthalocyanine obtained in Example 3, 70 ml of water and 100 ml of 1,1,2-trichloroethane was heated to 45° to 50° C. Then, a mixed solution comprising 19.5 g (84 mmol) of sulfuryl chloride and 10 ml of 1,1,2-trichloroethane was added thereto dropwise in 50 minutes at the same temperature, followed by reaction for 2 hours at the same temperature. After completion of the reaction, the reaction mixture was neutralized with 180 g of a 10% aqueous sodium hydroxide solution, to which 1.5 liters of toluene were subsequently added for extraction. The mixture thus obtained was separated into two phases, and the organic phase was washed with 400 ml of water twice. Then, the solvent was distilled off the organic phase to obtain a precipitate. After drying, the precipitate was purified by column chromatography (silica gel 1.0 kg, solvent=toluene:hexane=1:1) to obtain 12 g of a dark green, chlorinated mixed phthalocyanine. The results of its maximum absorption wavelength ($\lambda_{max}$) and gram extinction coefficient ($\epsilon_g$) are as follows:

$\lambda_{max}$=704.5 nm, $\epsilon_g$=1.4×10$^5$ cm$^2$/g (solvent:toluene)

Using the above-described chlorinated mixed phthalocyanine, a CD-R medium was prepared in the same manner as in Example 1. When an EFM signal was written in the medium at a linear velocity of 1.3 m/sec with a power of 6.0 mW by means of a semiconductor laser of 780 nm, the error rate was less than 10.

EXAMPLE 5

Ten grams of a dark green, brominated mixed phthalocyanine were obtained in the same manner as in Example 1, except that 20 g (61.7 mmol) of the phthalonitrile derivative given by formula (3-1) and 14.4 g (61.7 mmol) of the phthalonitrile derivative given by formula (4-1) were used. The results of its maximum absorption wavelength ($\lambda_{max}$) and gram extinction coefficient ($\epsilon_g$) are as follows:

$\lambda_{max}$=714.0 nm, $\epsilon_g$=1.4×10$^5$ cm$^2$/g (solvent=toluene)

Using the above-described brominated mixed phthalocyanine, a CD-R medium was prepared in the same manner as in Example 1. When an EFM signal was written in the medium at a linear velocity of 1.3 m/sec with a power of 6.0 mW by means of a semiconductor laser of 780 nm, the error rate was less than 10.

COMPARATIVE EXAMPLE 1

Using an illustrated compound in Japanese Patent Laid-Open No. 62878/1991 (U.S. Pat. No. 5,124,067) given by the following formula (A), a medium was prepared in the same manner as in Example 1 and evaluated.

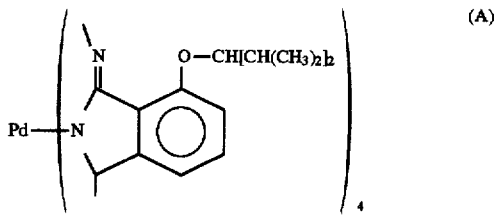

(A)

It needed a power of 10 mW to write an EFM signal in the medium at a linear velocity of 1.3 m/sec by means of a semiconductor laser of 780 nm. The error rate at that time was 12.

EXAMPLES 6–16

Phthalocyanine compounds given in Table 1 were synthesized in the same manner as in Example 1. Table 1 shows the structures and molar ratio of the phthalonitrile derivatives represented by formulae (3) and (4) used for the synthesis of the phthalocyanine compound of each Examples, the kind and number of the halogen atom substituted, the kind of the central metal, and the maximum absorption wavelength ($\lambda_{max}$:nm) and gram extinction coefficient ($\epsilon_g \times 10^5$) of the synthesized phthalocyanine in a toluene solution. In each Example, a CD-R medium was prepared in the same manner as in Example 1, and using a semiconductor laser of 780 nm, the laser power (mW) necessary to write an EFM signal at a linear velocity of 1.3 m/sec was measured, and the error rate at that time was evaluated. In the evaluation of the error rate, "A" denotes an error rate of less than 10, "B" whereas signifies an error rate of 10 or more. The results are shown in Table 1.

EXAMPLES 17–27

Phthalocyanine compounds given in Table 2 were synthesized in the same manner as in Example 3. Table 2 shows the structures and molar ratio of the diiminoisoindoline derivatives represented by formulae (5) and (6) used for the synthesis of the phthalocyanine compound of each Examples, the kind and number of the halogen atom substituted, the kind of the central metal, and the maximum absorption wavelength ($\lambda_{max}$:nm) and gram extinction coefficient ($\epsilon_g \times 10^5$) of the synthesized phthalocyanine compound in a toluene solution. In each Example, a CD-R medium was prepared in the same manner as in Example 1, and using a semiconductor laser of 780 nm, the laser power (mW) necessary to write an EFM signal at a linear velocity of 1.3 m/sec was measured, and the error rate at that time was evaluated. In the evaluation of the error rate, "A" denotes an error rate of less than 10, whereas "B" signifies an error rate of 10 or more. The results are shown in Table 2.

TABLE 1

| | Formula (3) | | Formula (4) |
|---|---|---|---|
| Example | $R^1$ | $R^{2'}$ | $R^3$ |
| 6 | —CH(CH$_3$)CH$_2$CH(CH$_3$)$_2$ | —C(CH$_3$)=CHCH$_3$ | —CH[CH(CH$_3$)$_2$]$_2$ |
| 7 | —CH(CH$_3$)CH$_2$CH(CH$_3$)$_2$ | —C(CH$_3$)=CHCH$_3$ | —CH[CH(CH$_3$)$_2$]$_2$ |
| 8 | —CH(CH$_3$)CH$_2$CH(CH$_3$)$_2$ | —CH=CHCH$_3$ | —CH[CH(CH$_3$)$_2$]$_2$ |
| 9 | —CH[CH(CH$_3$)$_2$]CH$_2$CH$_3$ | —CH=CHCH$_3$ | —CH(CH$_3$)CH$_2$CH(CH$_3$)$_2$ |
| 10 | —CH[CH(CH$_3$)$_2$]CH$_2$CH$_3$ | —CH=CHCH$_2$CH(CH$_3$)$_2$ | —CH(CH$_3$)CH$_2$CH(CH$_3$)$_2$ |
| 11 | —CH[CH(CH$_3$)$_2$]CH$_2$CH$_3$ | —CH—CHCH$_2$CH(CH$_3$)$_2$ | —CH(CH$_3$)CH$_2$CH(CH$_3$)$_2$ |
| 12 | —CH[CH(CH$_3$)$_2$]$_2$ | —CH=CHCH$_3$ | —CH[CH(CH$_3$)$_2$]$_2$ |
| 13 | —CH(CH$_3$)CH$_2$CH(CH$_3$)$_2$ | —CH(C$_2$H$_5$)CH=CHCH(CH$_3$)$_2$ | —CH[CH(CH$_3$)$_2$]$_2$ |
| 14 | —CH(CH$_3$)CH$_2$CH(CH$_3$)$_2$ | —CH(C$_2$H$_5$)CH=CHCH(CH$_3$)$_2$ | —CH[CH(CH$_3$)$_2$]$_2$ |
| 15 | —CH$_2$CH(CH$_3$)$_2$ | —CH=CHCH$_3$ | —CH[CH(CH$_3$)$_2$]$_2$ |
| 16 | —CH[CH(CH$_3$)$_2$]$_2$ | —CH=CHCH$_3$ | —CH[CH(CH$_3$)$_2$]$_2$ |

| Example | Molar ratio (3):(4) | X | n | Central metal | $\lambda_{max}$ nm | $\epsilon \times 10^5$ | Writing power (mW) | Error rate |
|---|---|---|---|---|---|---|---|---|
| 6 | 1:1 | Br | 6.0 | Pd | 714.0 | 1.3 | 4.5 | A |
| 7 | 1:15 | Cl | 9.0 | Cu | 724.0 | 1.5 | 6.0 | A |
| 8 | 1:10 | Cl | 10.5 | Pd | 713.5 | 1.4 | 6.0 | A |
| 9 | 1:3 | Br | 5.7 | Pd | 714.0 | 1.4 | 6.0 | A |
| 10 | 1:4 | Cl | 8.0 | Cu | 723.5 | 1.4 | 5.0 | A |
| 11 | 1:1 | I | 3.5 | Pd | 718.0 | 1.1 | 5.0 | A |
| 12 | 1:3 | Br | 6.5 | Pd | 714.0 | 1.4 | 6.5 | A |
| 13 | 1:1 | Br | 5.8 | Pd | 713.5 | 1.3 | 5.5 | A |
| 14 | 1:8 | I | 2.0 | Cu | 728.0 | 1.0 | 5.0 | A |
| 15 | 1:4 | Br | 5.8 | Pd | 713.5 | 1.4 | 5.5 | A |
| 16 | 1:2 | Br | 6.0 | Pd | 714.5 | 1.3 | 5.0 | A |

TABLE 2

| Example | Formula (3) R¹ | R² | Formula (4) R³ |
|---|---|---|---|
| 17 | —CH$_2$CH$_2$CH(CH$_3$)$_2$ | —CH=CHCH$_2$CH$_2$CH$_3$ | —CH(CH$_3$)CH$_2$CH(CH$_3$)$_2$ |
| 18 | -(CH$_2$)$_3$CH$_3$ | —CH=CHCH$_3$ | —CH[CH(CH$_3$)$_2$]$_2$ |
| 19 | —CH(CH$_3$)CH$_2$CH$_2$CH$_3$ | —C(CH$_3$)=CHCH$_2$CH$_3$ | —CH[CH(CH$_3$)$_2$]$_2$ |
| 20 | —CH(CH$_3$)CH$_2$CH$_3$ | —CH=CHCH$_3$ | —CH[CH(CH$_3$)$_2$]CH$_2$CH$_3$ |
| 21 | -(CH$_2$)$_3$CH$_3$ | —CH=CHCH$_2$CH(CH$_3$)$_2$ | —CH[CH(CH$_3$)$_2$]$_2$ |
| 22 | -(CH$_2$)$_3$CH$_3$ | —CH=CHCH$_2$CH(CH$_3$)$_2$ | —CH(CH$_3$)CH$_2$CH(CH$_3$)$_2$ |
| 23 | —CH[CH(CH$_3$)$_2$]$_2$ | —CH=CHCH$_3$ | —CH[CH(CH$_3$)$_2$]$_2$ |
| 24 | —CH(CH$_3$)CH$_2$CH(CH$_3$)$_2$ | —C(CH$_3$)=CHCH$_3$ | -(CH$_2$)$_3$CH$_3$ |
| 25 | -cyclo-C$_6$H$_{11}$ | —CH=CHCH$_3$ | —CH$_2$CH$_2$OCH$_2$OCH$_3$ |
| 26 | —CH$_2$CH(CH$_3$)$_2$ | —CH=CHCH$_3$ | —CH(CF$_3$)$_2$ |
| 27 | —CH[CH(CH$_3$)$_2$]$_2$ | —CH=CHCH$_2$CH(CH$_3$)$_2$ | —CH[CH(CH$_3$)$_2$]$_2$ |

| Example | Molar ratio (3):(4) | X | n | Central metal | $\lambda_{max}$ nm | $\epsilon \times 10^5$ | Writing power (mW) | Error rate |
|---|---|---|---|---|---|---|---|---|
| 17 | 1:4 | Br | 2.5 | Mg | 700.0 | 1.6 | 5.5 | A |
| 18 | 1:15 | Br | 3.2 | Co | 698.0 | 1.7 | 6.0 | A |
| 19 | 1:1 | Cl | 7.0 | Pt | 701.5 | 1.4 | 6.0 | A |
| 20 | 1:4 | Cl | 1.0 | SiCl$_2$ | 723.0 | 1.5 | 5.5 | A |
| 21 | 1:3 | Br | 1.5 | VO | 735.0 | 1.5 | 5.0 | A |
| 22 | 1:8 | Br | 5.5 | Ni | 711.0 | 1.4 | 6.0 | A |
| 23 | 1:1 | I | 4.0 | Pd | 725.0 | 1.1 | 6.5 | A |
| 24 | 1:1 | Br | 3.7 | Zn | 704.0 | 1.6 | 5.5 | A |
| 25 | 1:3 | Cl | 2.0 | Pd | 714.0 | 1.5 | 6.0 | A |
| 26 | 1:8 | Br | 5.8 | Pd | 713.5 | 1.4 | 5.5 | A |
| 27 | 1:1 | Cl | 10.0 | Cu | 720.0 | 1.2 | 5.0 | A |

What is claimed is:

1. A phthalocyanine compound represented by the following formula (1):

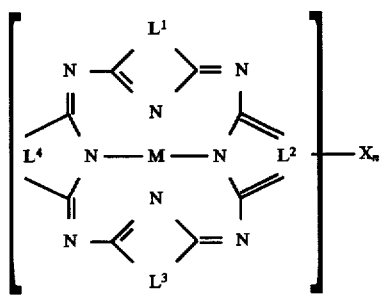
(1)

wherein in formula (1), M is two hydrogen atoms, a divalent metallic atom, a trivalent monosubstituted metallic atom, a tetravalent disubstituted metallic atom or an oxymetal atom, and L$^1$, L$^2$, L$^3$ and L$^4$ are each independently formula (a) or (b):

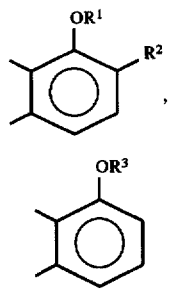

wherein in formula (a) or (b), R$^1$ and R$^3$ are each a substituted or unsubstituted alkyl group, and R$^2$ is a straight chain or branched halogenated alkyl or alkenyl group having 3 to 10 carbon atoms, X is a chlorine, bromine or iodine atom, and n is an integer of 1 to 11, provided that at least one of L$^1$, L$^2$, L$^3$ and L$^4$ is formula (a), but all of L$^1$ to L$^4$ are not formula (a) at the same time.

2. The phthalocyanine compound according to claim 1 wherein M in the formula (1) is Pd, Cu, Ru, Pt, Ni, Co, Rh, Zn, VO, TiO, Si(Y)$_2$, Sn(Y)$_2$ or Ge(Y)$_2$ (wherein Y is a halogen atom, alkoxy group, aryloxy group, acyloxy group, hydroxy group, alkyl group, aryl group, alkylthio group, arylthio group, trialkylsilyloxy group, trialkyltinoxy group or trialkylgermaniumoxy group).

3. A near infrared light-absorbing dye comprising a phthalocyanine mixture represented by the following formula (2):

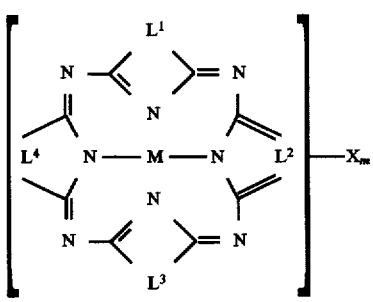
(2)

wherein in formula (2), M is two hydrogen atoms, a divalent metallic atom, a trivalent monosubstituted metallic atom, a tetravalent disubstituted metallic atom or an oxymetal atom, and L$^1$, L$^2$, L$^3$ and L$^4$ are each independently formula (a) or (b):

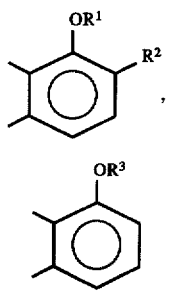 (a)

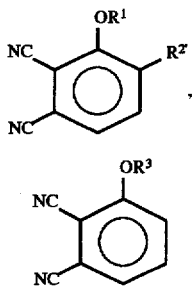 (b)

wherein in formula (a) or (b), $R^1$ and $R^3$ are each a substituted or unsubstituted alkyl group, and $R^2$ is a straight chain or branched halogenated alkyl or alkenyl group having 3 to 10 carbon atoms, X is a chlorine, bromine or iodine atom, and m is an integer of 1 to 12, provided that formula (2) denotes a mixture of $L^1=L^2=L^3=L^4$=formula (a), $L^1=L^2=L^4$=formula (a) and $L^3$=formula (b), $L^1=L^4$=formula (a) and $L^2=L^3$=formula (b), $L^1=L^3$=formula (a) and $L^2=L^4$=formula (b), $L^2=L^3=L^4$= formula (b) and $L^1$=formula (a), and $L^1=L^2=L^3=L^4$=formula (b).

4. The near infrared light-absorbing dye according to claim 3 wherein M in formula (2) is Pd, Cu, Ru, Pt, Ni, Co, Rh, Zn, VO, TiO, $Si(Y)_2$, $Sn(Y)_2$ or $Ge(Y)_2$ (wherein Y is a halogen atom, alkoxy group, aryloxy group, acyloxy group, hydroxy group, alkyl group, aryl group, alkylthio group, arylthio group, trialkylsilyloxy group, trialkyltinoxy group or trialkylgermaniumoxy group).

5. A process for preparing the dye according to claim 3 comprising reacting formula (3) with formula (4) in a molar ratio of 1:1–15 in the presence or absence of a metallic compound and reacting the reaction product with a halogenating agent,

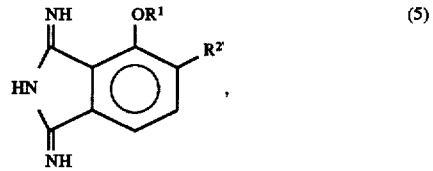 (3)

(4)

wherein $R^1$ and $R^3$ is a substituted or unsubstituted alkyl group, and $R^{2'}$ is straight chain or branched alkenyl group having 3 to 10 carbon atoms.

6. A dye obtained by the process according to claim 5.

7. A process for preparing the dye according to claim 3 comprising reacting formula (5) with formula (6) in a molar ratio of 1:1–15 in the presence or absence of a metallic compound and reacting the reaction product with a halogenating agent,

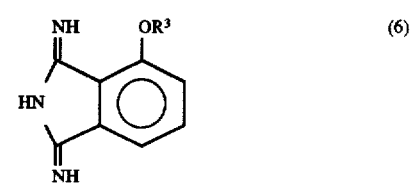 (5)

(6)

wherein $R^1$ and $R^3$ are each a substituted or unsubstituted alkyl group, and $R^{2'}$ is a straight chain or branched alkenyl group having 3 to 10 carbon atoms.

8. A dye obtained by the process according to claim 7.

9. An optical recording medium comprising the near infrared light-absorbing dye according to claim 3.

10. The optical recording medium according to claim 9 having a constitution in which a recording layer containing the near infrared light-absorbing dye, a reflective layer made of gold or aluminum and a protective layer are laminated in this order on a substrate.

* * * * *